United States Patent
Her

(10) Patent No.: US 10,610,670 B2
(45) Date of Patent: Apr. 7, 2020

(54) CATHETER FIXTURE

(71) Applicant: SMHERS, Paju-si, Gyeonggi-do (KR)

(72) Inventor: Yun-Hee Her, Seoul (KR)

(73) Assignee: SMHERS, Paju-si, Gyeonggi-Do (KR)

( * ) Notice: Subject to any disclaimer, the term of this patent is extended or adjusted under 35 U.S.C. 154(b) by 103 days.

(21) Appl. No.: 15/750,670

(22) PCT Filed: Apr. 1, 2016

(86) PCT No.: PCT/KR2016/003422
§ 371 (c)(1),
(2) Date: Feb. 6, 2018

(87) PCT Pub. No.: WO2017/022924
PCT Pub. Date: Feb. 9, 2017

(65) Prior Publication Data
US 2018/0236206 A1   Aug. 23, 2018

(30) Foreign Application Priority Data
Aug. 6, 2015   (KR) ........................ 10-2015-0111051

(51) Int. Cl.
*A61M 5/32* (2006.01)
*A61M 25/02* (2006.01)
*A61J 15/00* (2006.01)

(52) U.S. Cl.
CPC .......... *A61M 25/02* (2013.01); *A61J 15/0053* (2013.01); *A61J 15/0015* (2013.01); *A61M 2025/028* (2013.01)

(58) Field of Classification Search
CPC .............. A61J 15/0053; A61J 15/0034; A61M 2025/028; A61M 25/02; A61M 2025/024; A61M 2025/0246; A61M 39/0247
See application file for complete search history.

(56) References Cited

U.S. PATENT DOCUMENTS

| 4,261,363 A | * | 4/1981 | Russo ................... A61M 25/02 |
|---|---|---|---|
| | | | 128/200.26 |
| 4,397,647 A | | 8/1983 | Gordon |
| 4,834,712 A | | 5/1989 | Quinn et al. |

(Continued)

FOREIGN PATENT DOCUMENTS

| JP | 08-038616 A | 2/1996 |
|---|---|---|
| JP | 2001-522664 A | 11/2001 |

(Continued)

*Primary Examiner* — Rebecca E Eisenberg
(74) *Attorney, Agent, or Firm* — Novick, Kim & Lee, PLLC; Jae Youn Kim

(57) ABSTRACT

Provided is a catheter fixture. The catheter fixture includes: a base plate having a base hole for passing a catheter; and a fixture body formed on a top of the base plate, and the fixture body having a first guide hole connected to the base hole, extending in an open direction of the base hole, and guiding the catheter and a second guide hole extending in a different direction from the first guide hole and guiding the catheter. Since the first guide hole and the second guide hole are formed in different directions in the catheter fixture, a user can extend the catheter in different directions if necessary. Accordingly, it is possible to more stably and simply prevent backflow of food or medicine, using one catheter fixture without a specific component.

4 Claims, 8 Drawing Sheets

(56) References Cited

U.S. PATENT DOCUMENTS

| | | | |
|---|---|---|---|
| 5,267,969 A | 12/1993 | Hirsch et al. | |
| 5,374,254 A | 12/1994 | Buma | |
| 6,482,183 B1 * | 11/2002 | Pausch | A61J 15/0015 |
| | | | 604/174 |
| 6,981,969 B2 * | 1/2006 | Chavez | A61M 25/02 |
| | | | 604/170.03 |
| 9,962,524 B2 * | 5/2018 | Andino | A61M 25/02 |
| 2010/0324491 A1 | 12/2010 | Bierman et al. | |

FOREIGN PATENT DOCUMENTS

| | | |
|---|---|---|
| JP | 2008-516656 A | 5/2008 |
| JP | 2010-088792 A | 4/2010 |
| KR | 10-1587015 B1 | 1/2016 |

* cited by examiner

CATHETER FIXTURE

TECHNICAL FIELD

The present invention relates to a catheter fixture and, more particularly, to a catheter fixture for fixing a catheter to the body of a patient.

BACKGROUND ART

A catheter, which is a kind of medical tubes, is widely used as a general name of tube-shaped instruments. There are catheters comprised of various materials and having various sizes and shapes for the usages. Such catheters may be used to extract retained substances in a body cavity or in various organs, absorb cleansing perfusate, measure the status of cardiac blood flow or central venous pressure, inject medicines or contrast media into a body, etc.

A Percutaneous Endoscopic Gastrostomy (PEG) tube, which is a kind of catheter, is a soft silicon tube designed to be inserted into the stomach through the abdomen and has an open port at the end thereof so that food can be injected. Further, as shown in FIG. 1, a fixture is combined with a PEG tube and guides the PEG tube in close contact with the skin of a patient.

After injecting medicine or food into a body through catheters including a gastrostomy tube, it is required to prevent backflow of the medicine or food through the catheters. To this end, a method of closing an end of a catheter protruding out of the body of a patient has been generally used to prevent backflow of medicine or food to the outside.

However, medicine or food may flow back to a closed end of a catheter, and in this case, there is a concern that food or medicine flows or is even ejected from the port at an end of the catheter, which should be protected from outside infection. In this case, it is difficult to expect actual effect in cleansing the port and the inside of the catheter by a manager (user) after injecting medicine, so prevention of backflow of food and medicine is required in terms of management and sanitation.

In the related art, as in FIG. 1, a catheter is maintained perpendicular to the body of a patient to inject food or medicine, and then it is bent at a right angle in any direction and then attached to the body of the patient by an adhesive band etc. to be stowed. In order to inject food or medicine again, the adhesive band is detached and then food or medicine is injected and catheters are managed in this way.

As described above, it is inconvenient to use catheters in the related art and it is dangerous in terms of sanitation to repeatedly attach and detach adhesive bands etc. to and from the skin, which is vulnerable to outside inspection of a patient. Further, a catheter attached to the body of a patient may be separated from the body of the patient when an adhesive band is detached.

In particular, the stomach wall and the inner fixture (not shown) of a catheter are usually slightly spaced from each other to prevent pressure that may be applied to the stomach wall, but when an adhesive such as an adhesive band is used, the danger that the catheter and the inner fixture are vertically pulled and press the stomach wall due to carelessness is increased.

DISCLOSURE

Technical Problem

The present invention has been made in an effort to solve the problems in the related art and an object of the present invention is to prevent backflow of food or medicine using a fixture for fixing a catheter.

Another object of the present invention is to keep a catheter bent in parallel with the skin of a patient using a catheter fixture even without using a specific adhesive such as an adhesive band.

Technical Solution

In order to achieve the objects of the present invention and aspect of the present invention provides a catheter fixture includes: a base plate having a base hole for passing a catheter; and a fixture body formed on a top of the base plate, and the fixture body having a first guide hole connected to the base hole, extending in an open direction of the base hole, and guiding the catheter, and a second guide hole extending in a different direction from the first guide hole and guiding the catheter.

The second guide hole may extend perpendicular to the first guide hole.

The second guide hole gradually declines as the second guide hole goes away from an end connected to the base hole.

The base plate and the fixture body may be integrally made of an elastic material.

The fixture body may have a guide fence protruding upward from a side of the base plate and a cover protruding upward from the base plate with an end directed back toward the base plate, the first guide hole may be formed between the guide fence and the cover, and the second guide hole may be formed between the cover and the base plate.

A side of the cover is open to the outside in the longitudinal direction of the second guide hole.

A third guide hole having a diameter different from the second guide hole may be formed through the guide fence to be open opposite to the second guide hole.

Advantageous Effects

The catheter fixture according to the present invention has the following effects.

Since the first guide hole and the second guide hole are formed in different directions in the catheter fixture, a user can extend the catheter in different directions, if necessary. For example, a user can guide a catheter vertically (through the first hole) when injecting food or medicine through the catheter, that is, guide a catheter in the insertion direction into the body of a patient, and can guide a portion of the catheter at a right angle (through the second guide hole) to prevent backflow after finishing injection. Accordingly, it is possible to more stably and simply prevent backflow of food or medicine, using one catheter fixture without a specific component, thereby improving convenience.

In particular, in the present invention, since the second guide hole of the catheter fixture gradually declines, it is possible to further reduce the possibility of backflow through a catheter. Further, since a side of the cover of the catheter fixture is open, it is possible to easily insert and take a catheter into and out of the second guide hole.

Further, by using the catheter fixture of the present invention, it is possible to stow a catheter at a right angle when not injecting food or medicine through the catheter, so there is no need to use a separate adhesive such as an adhesive band. Accordingly, it is possible to more easily manage a catheter, improve sanitation, and prevent the possibility of excessive pressure on the body of a patient when detaching an adhesive, so stability is also improved.

MODE FOR INVENTION

Figure 1:
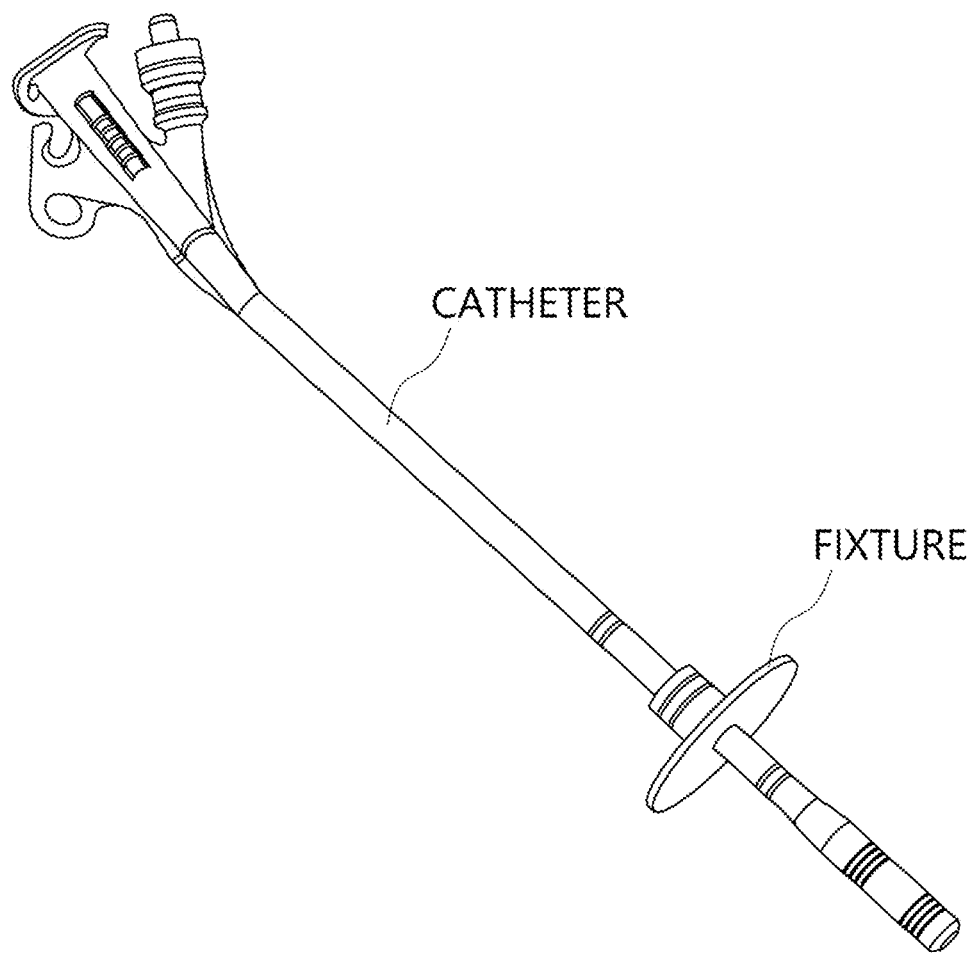
FIG. 1 is a perspective view showing a common catheter and catheter fixture.

Hereinafter, embodiments of the present invention are described in detail with exemplary drawings. When components are given reference numerals in the drawings, the same components are given the same reference numerals even if they are shown in different drawings. Further, in the following description of embodiments of the present invention, when a detailed description of well-known configurations or functions is determined as interfering with understanding of the embodiments of the present invention, they are not described in detail.

Further, terms 'first', 'second', 'A', 'B', '(a)', and '(b)' can be used in the following description of embodiments of the present invention. The terms are provided only for discriminating components from other components, and the essence, sequence, or order of the components are not limited by the terms. When a component is described as being "connected", "combined", or "coupled" with another component, it should be understood that the component may be connected or coupled to another component directly or with another component interposing therebetween.

A catheter fixture for a PEG tube of catheters T is exemplified in the following description. Obviously, the catheter T according to the present invention may be applied all of various catheters T.

A catheter T is described first for the convenience of description. The catheter T, which is a kind of medical tube, is made of a flexible material such that a portion is inserted into the body of a patient and the other portion is left outside the body. A syringe etc. is connected to the portion of the catheter T left outside the body of the patient to inject medicine or food into the body through the catheter T.

A catheter fixture is combined with the catheter T. The catheter fixture allows the catheter T to be fixed to a portion of the body of a patient and they may be combined by fitting the catheter T through the fixture.

Figure 2:
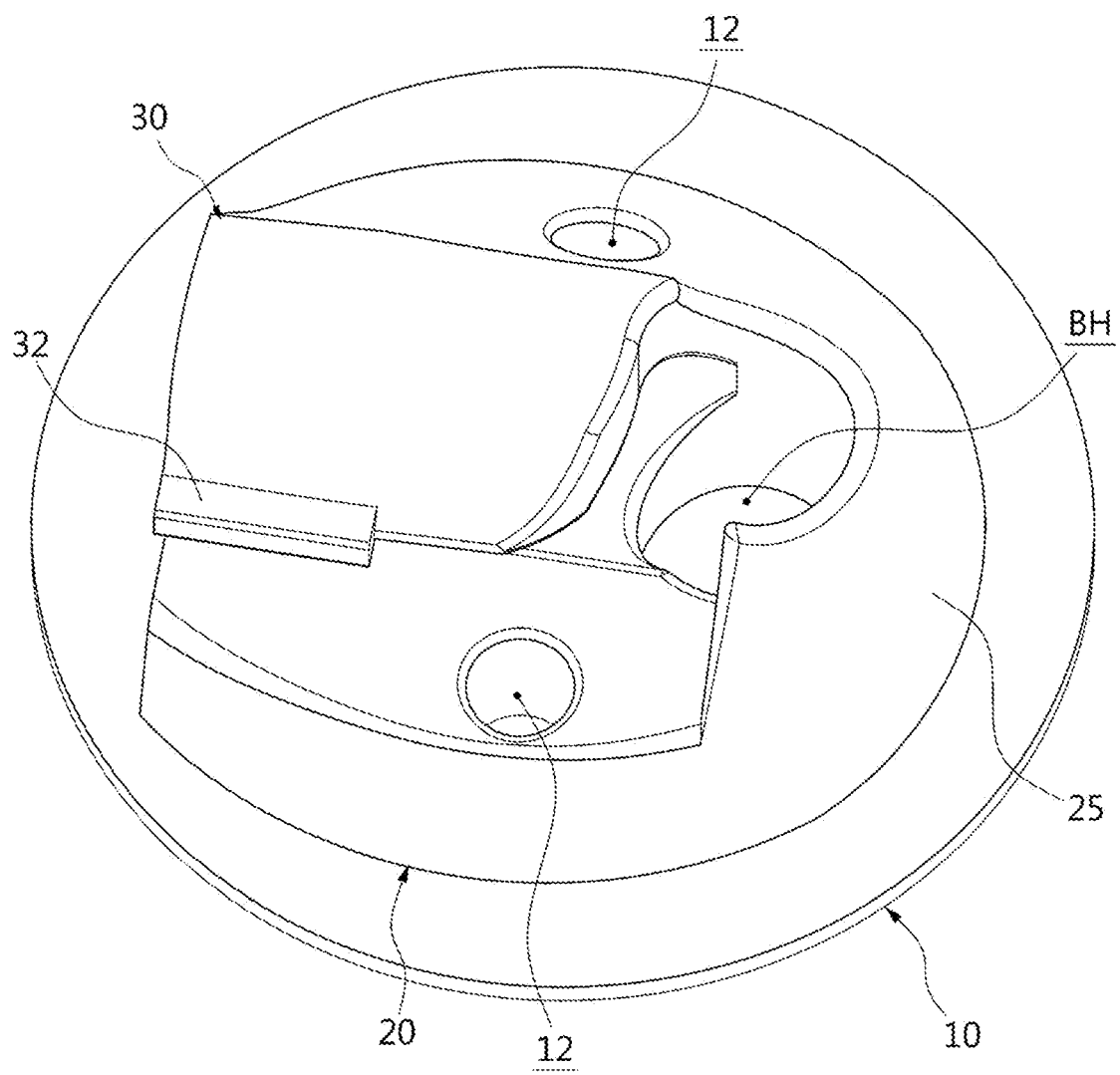
FIG. 2 is a perspective view showing an embodiment of a catheter fixture according to the present invention.

The catheter fixture is clearly shown in the perspective view of FIG. 2. As shown in the figure, the frame of the catheter fixture is formed by a base plate 10. The base plate 10 is a substantially thin plate and is a part to be actually brought in contact with the skin of a patient. Obviously, a gauze etc. may be inserted between the base plate 10 and the skin of a patient. In this embodiment, although the base plate 10 is a circular plate, but it is not limited thereto and may be formed in various shapes of plates such as an ellipse or a polygon.

A base hole BH is formed through the base plate 10. The base hole BH, which is a part through which the catheter T passes, has an inner diameter the same as or larger than the outer diameter of the catheter T. The base hole BH is formed vertically through the base plate 10.

The fixture body 20 is formed on the top of the base plate 10. The fixture body 20 is integrally formed with the base plate 10, protruding at a predetermined height from the base plate 10. That is, the base plate 10 and the fixture body 20 are made of the same material in one unit, and they are made of silicon in this embodiment. The catheter fixture may be made of flexible materials such as silicon.

The fixture body 20 has a guide fence 25 at a side. The guide fence 25 protrudes upward from a side of the base plate 10. The guide fence 25 supports a side of the catheter T extending vertically through a first guide hole GH1 to be described below or moving horizontally through a second guide hole GH2.

Figure 7:
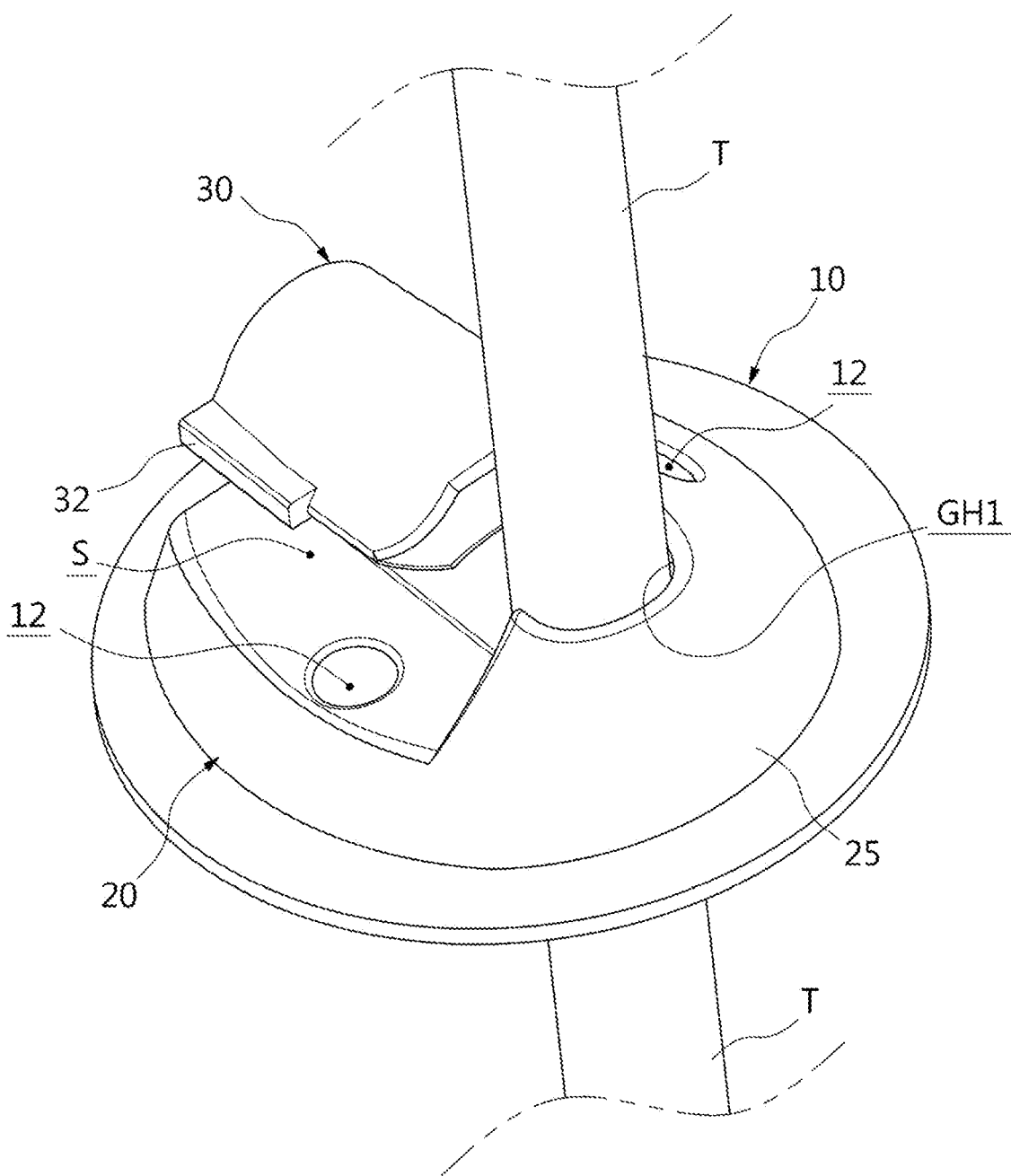
FIG. 7 is a perspective view showing a catheter guided upward by an embodiment of a catheter fixture according to the present invention.

The guide fence 25 is formed close to the base hole BH and the first guide hole GH1 connected to the base hole BH is vertically formed at a side of the guide fence 25. More accurately, the first guide hole GH 1 is formed between the guide fence 25 and a cover 30 to be described below. The first guide hole GH1 is connected to the base hole BH and extends in the open direction of the base hole BH1, so, as shown in FIG. 7, when the catheter T passes through the first guide hole GH1, the catheter T can extend in the insertion direction into the body of a patient. In this state, medicine or food can be injected from an end of the catheter T.

Figure 4:
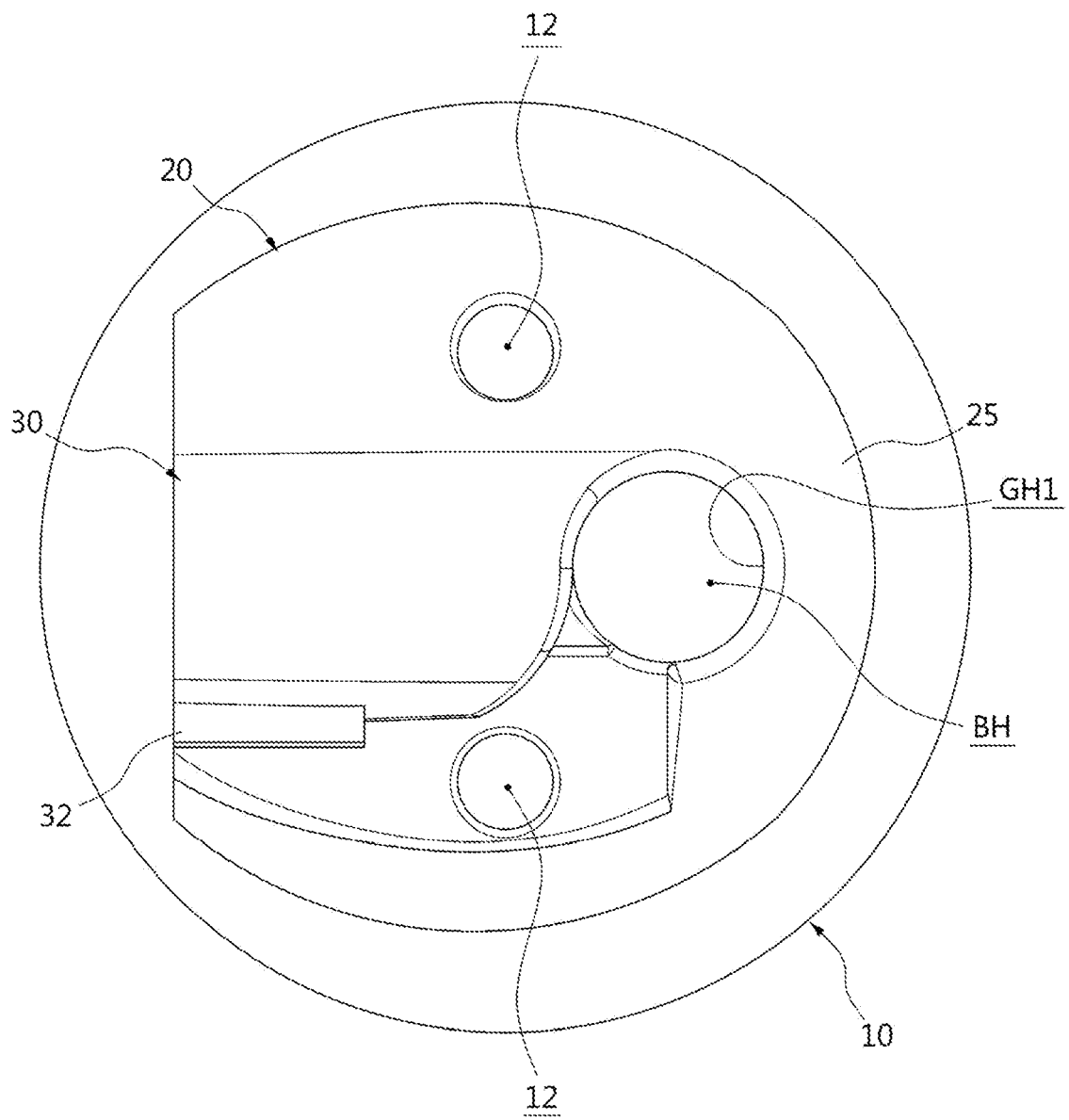
FIG. 4 is a plan view showing an embodiment of the catheter fixture according to the present invention.
Figure 5:
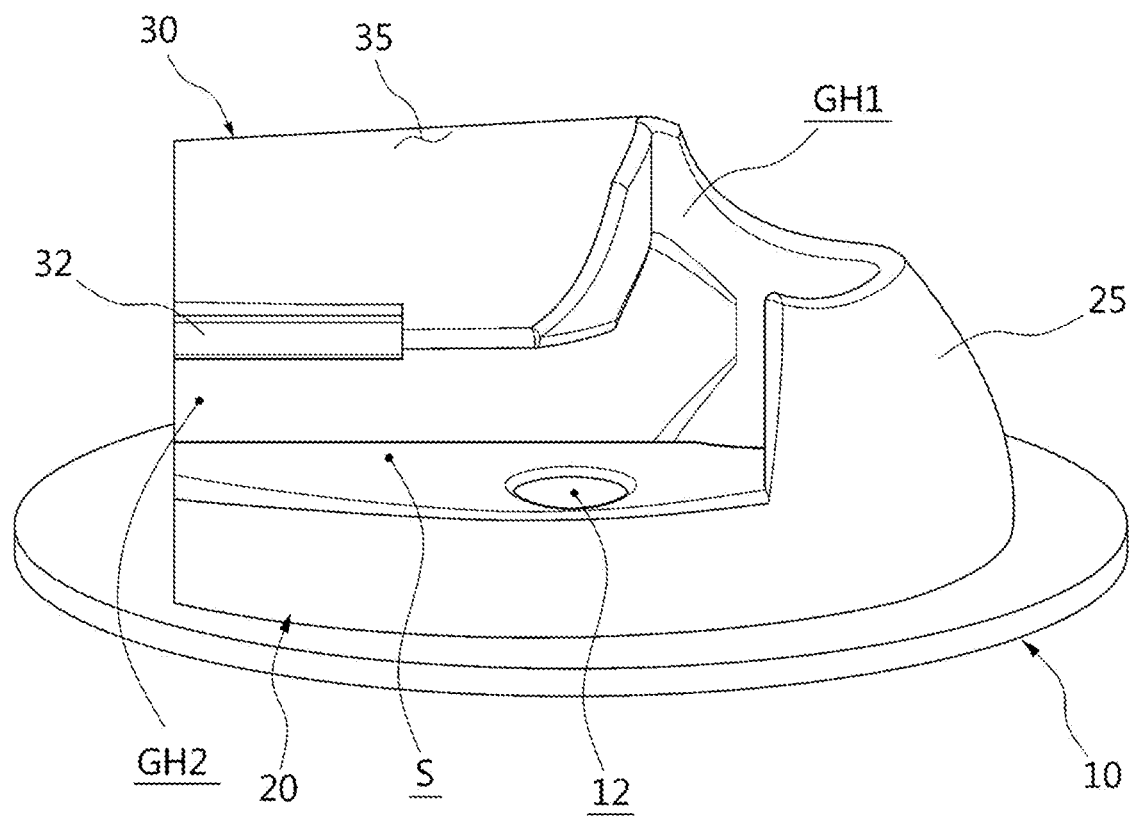
FIG. 5 is a side view showing an embodiment of the catheter fixture according to the present invention.

The cover 30 is formed at a side of the guide fence 25. The cover 30 protrudes upward from the base plate 10 with one end directed back toward the base plate 10. That is, the cover 30 is rounded such that the outer surface curved and covers the second guide hole GH2 thereunder. As shown in FIGS. 4 and 5, the cover 30 may continue from the guide fence 25.

The cover 30 forms the second guide hole GH2 and holds the upper surface of the catheter T guided through the second guide hole GH2 to prevent the catheter T from separating from the second guide hole GH2. That is, the second guide hole GH2 is formed between the cover 30 and the base plate 10.

Figure 6A:
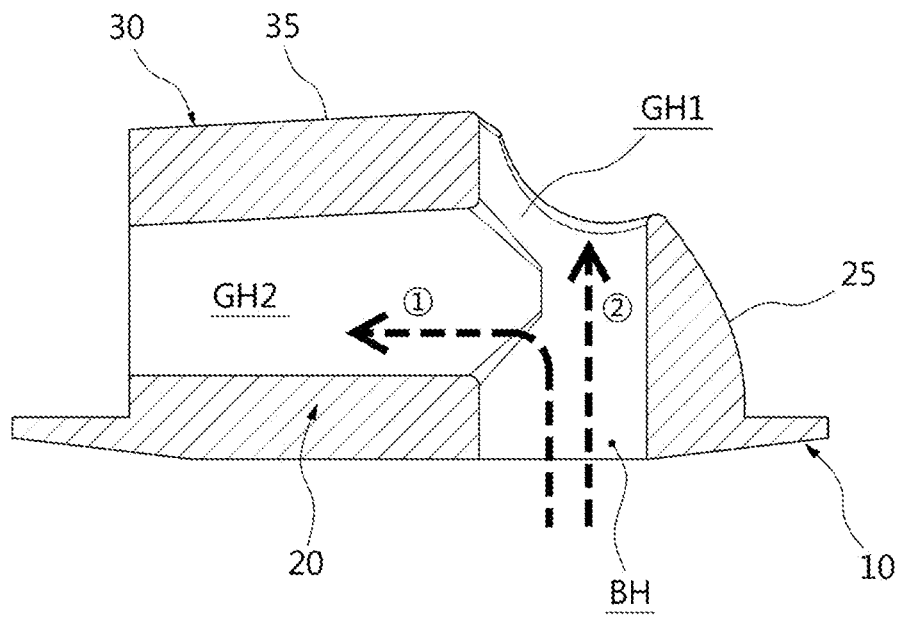
FIGS. 6a and 6b are vertical cross-sectional views showing the internal structures of two different catheter fixtures according to the present invention.
Figure 6B:
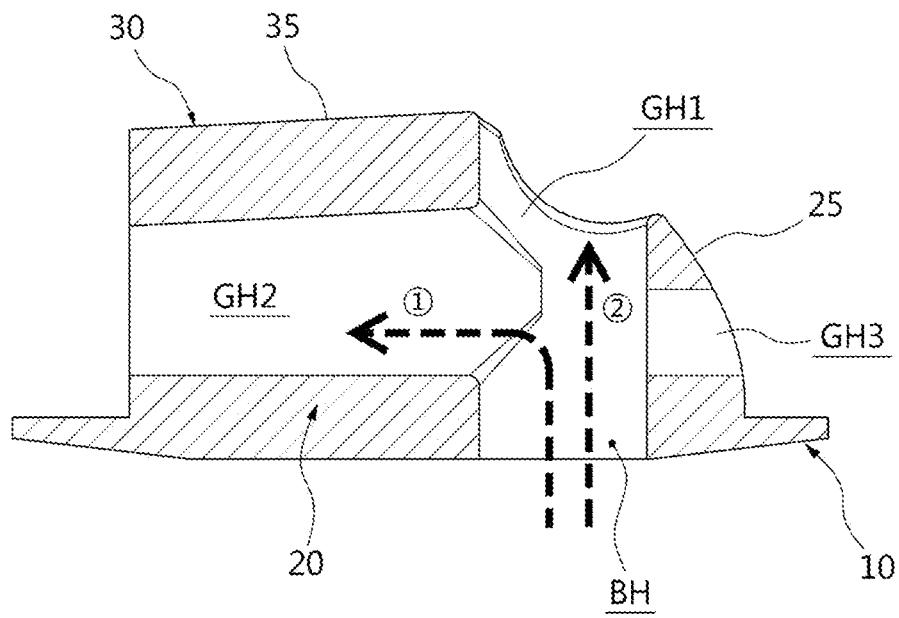

As shown in FIG. 6a, the second guide hole GH2 gradually declines as it goes away from the end connected to the base hole BH. In this embodiment, the top 35 of the cover 30 gradually declines as it goes away from the guide fence 25, so the guide hole GH2 also declines. Accordingly, the catheter T can be bent slight down from the right angle when passing through the second guide hole GH2, so backflow through the catheter T can be more stably prevented.

The catheter T passing through the declining second guide hole GH2 is naturally guided gradually closer to the skin of a patient, so the catheter T can be easily fixed to the patient's skin. For reference, in FIG. 6a, the arrow ① indicates the direction in which the catheter T is guided into the second guide hole GH2 and the arrow ② indicates the direction in which the catheter T is guided into the first guide hole GH1.

Figure 3:
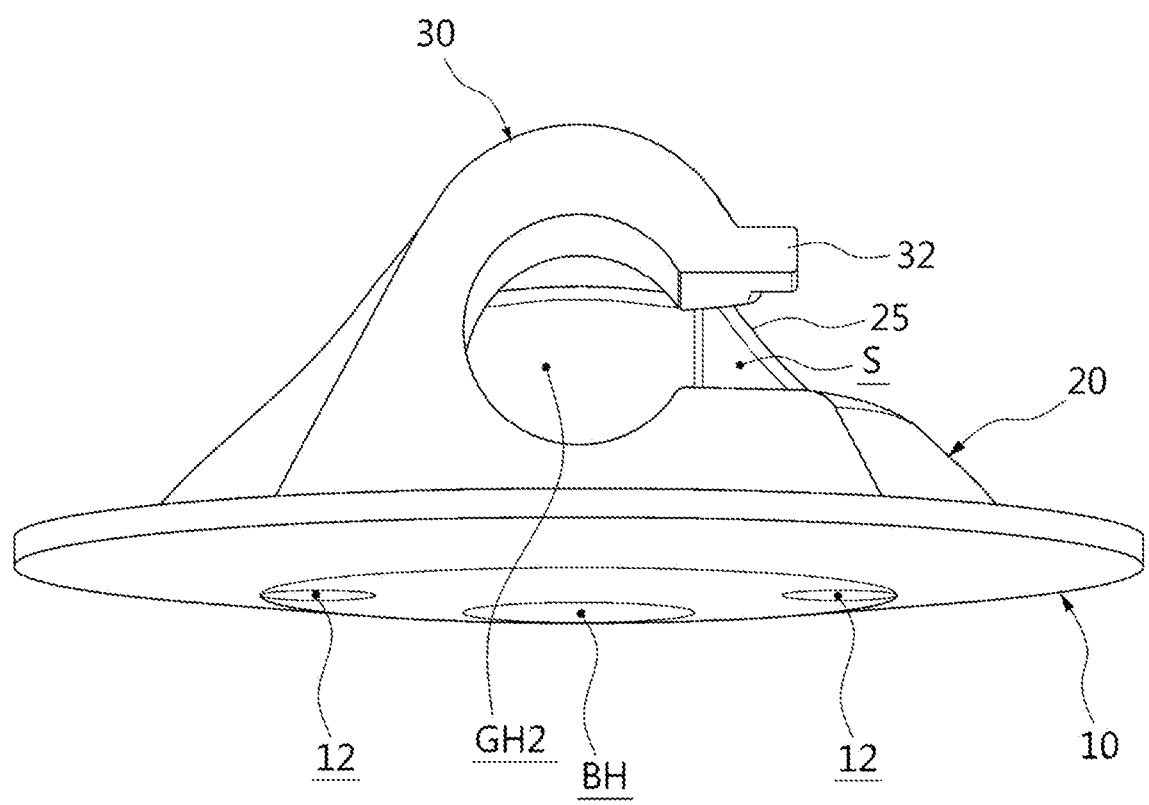
FIG. 3 is a front view showing an embodiment of the catheter fixture according to the present invention.

As shown in FIGS. 3 and 5, the second guide hole GH2 is laterally open. That is, a predetermined space S is defined between the cover 30 and the fixture body 20, so a portion of the second guide hole GH2 is open to the outside. Further, a portion of the catheter T can be easily inserted into and taken out of the second guide hole GH2 through the space S.

Since the catheter fixture is made of a flexible material in this embodiment, a user can open the second guide hole GH2 by holding and opening an end of the cover 30 upward (in FIG. 5) from the space S and then insert or take the catheter T into or out of the second guide hole GH2.

A projective grip 32 is formed at a side of the cover 30. The projective grip 32 protrudes from a side of the cover 30 perpendicular to the longitudinal direction of the second guide hole GH2 so that a user can easily open the cover 30 by holding it.

As shown in FIG. 5, the guide fence 25 may protrude from the base plate 10 less than the cover 30. This is for more easily handling an end of the catheter T through the gap formed by the height difference between the cover 30 and the guide fence 25.

Meanwhile, as shown in FIG. 6a, a third guide hole GH3 may be formed through the guide fence 25 to be open to the outside opposite to the second guide hole GH2. The third guide hole GH3 allows the catheter T to extend opposite to the second guide hole GH2. The third guide hole GH3 may have a different diameter from the second guide hole GH2 so that the catheter fixture can be applied to catheters T having various diameters. Non-stated reference numeral '12' indicates through-holes formed through the base plate 10 and the fixture body. The through-holes 12 decrease the contact area between the skin of a patient and the catheter fixture and increase the contact area between the skin of a patient and air.

A process of using the catheter fixture according to the present invention is described hereafter.

First, a user inserts a portion of the catheter T into the body of a patient and then fixes the catheter fixture on the patient's skin. In this state, the catheter T exposed out of the patient's body extends through the first guide hole GH1 of the catheter fixture, that is, as shown in FIG. 7, the catheter T extends vertically through the first guide hole GH1.

In this state, food or medicine is injected from a first end of the catheter T and is supplied into the patient's body through the catheter T.

When injection of food or medicine is finished, the user blocks the first end and puts the catheter T into the second guide hole GH2. In more detail, when the cover 30 of the catheter fixture is elastically deformed and the space S between the cover 30 and the base plate 10, that is, the inlet of the second guide hole GH2 is widened, the catheter T can be easily inserted into the second guide hole GH2.

Figure 8:
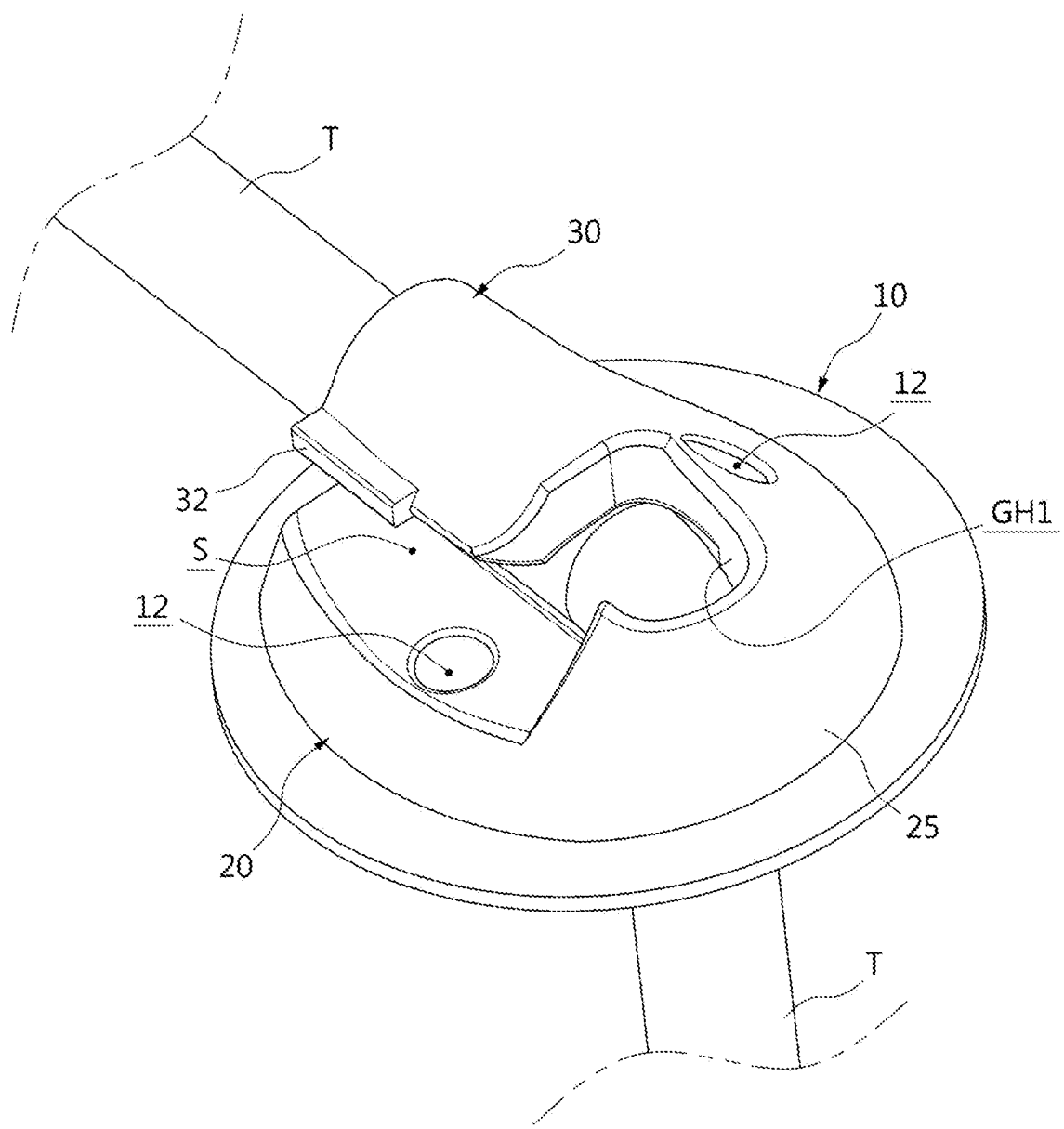
FIG. 8 is a perspective view showing that a catheter is guided at a right angle by an embodiment of a catheter fixture according to the present invention.

Accordingly, as shown in FIG. 8, the catheter T is partially bent at a right angle and backflow of the food or medicine can be more stably prevented at the bent portion. Further, since the catheter T extends in parallel with the patient's skin by the catheter fixture, the user can more easily fix a portion of the catheter T to the patient's skin after finishing injecting food or medicine.

If necessary, the user may fix the base plate 10 to the patient's skin using an adhesive such as an adhesive tape.

As described above, according to the present invention, since it is possible to extend the catheter T using one catheter fixture, it is possible to inject food or medicine through the catheter T and prevent backflow of the food or medicine.

Even if all components of the embodiments of the present invention were described as being combined in a single unit or operated in combination with each other, the present invention is not limited to the embodiments. That is, one or more of all components may be selectively combined to operate within the scope of the present invention. Further, the terms "comprise", "include", "have", etc. when used in this specification mean that the components can exist unless specifically stated otherwise, so they should be construed as being able to further include other components. Unless otherwise defined, all terms including technical and scientific terms used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The above description merely explains the spirit of the present invention and the present invention may be changed and modified in various ways without departing from the spirit of the present invention by those skilled in the art. Accordingly, the embodiments described herein are provided merely not to limit, but to explain the spirit of the present invention, and the spirit of the present invention is not limited by the embodiments. The patent right of the present invention should be construed by the following claims and the scope and spirit of the invention should be construed as being included in the patent right of the present invention.

The invention claimed is:

1. A catheter fixture comprising:
 a base plate having a base hole through which a catheter is capable of passing; and
 a fixture body disposed on a top of the base plate, the fixture body having a first guide hole communicating with the base hole and extending in a first direction from the base hole for guiding the catheter, and a second guide hole extending in a second direction different from the first direction of the first guide hole for guiding the catheter in the second direction from the first guide hole,
 wherein the base plate and the fixture body are integrally made of an elastic material,
 wherein the fixture body has a guide fence protruding upward from the base plate and a cover disposed adjacent to the guide fence, and the first guide hole is disposed between the guide fence and the cover, and
 wherein the cover protrudes upward from the base plate and has an end portion extending downward towards the base plate, and a space is defined between the end portion directed toward the base plate and the base plate such that the second guide hole is laterally open.

2. The catheter fixture of claim 1, wherein the second guide hole extends perpendicular to the first guide hole.

3. The catheter fixture of claim 1, wherein the second guide hole gradually declines toward the base plate as the second guide hole goes away from an end thereof connected to the base hole.

4. The catheter fixture of claim 1, wherein a third guide hole having a diameter different from the second guide hole penetrates through the guide fence to be open in an opposite direction from the second guide hole.

* * * * *